United States Patent
Kroeker et al.

(10) Patent No.: US 12,216,187 B2
(45) Date of Patent: Feb. 4, 2025

(54) CORRECTING OBJECT MOVEMENT DURING MR IMAGING

(71) Applicant: Siemens Healthcare GmbH, Erlangen (DE)

(72) Inventors: Randall Kroeker, Erlangen (DE); Daniel Kraus, Möhrendorf (DE); Michael Roas-Löffler, Erlangen (DE); Wilfried Schnell, Forchheim (DE); Daniel Nicolas Splitthoff, Uttenreuth (DE)

(73) Assignee: Siemens Healthineers AG, Forchheim (DE)

( * ) Notice: Subject to any disclaimer, the term of this patent is extended or adjusted under 35 U.S.C. 154(b) by 531 days.

(21) Appl. No.: 17/225,350

(22) Filed: Apr. 8, 2021

(65) Prior Publication Data
US 2021/0325501 A1  Oct. 21, 2021

(30) Foreign Application Priority Data
Apr. 16, 2020  (EP) .................................... 20169738

(51) Int. Cl.
*G01R 33/565* (2006.01)
*A61B 5/055* (2006.01)
(Continued)

(52) U.S. Cl.
CPC ........ *G01R 33/56509* (2013.01); *A61B 5/055* (2013.01); *A61B 5/1127* (2013.01);
(Continued)

(58) Field of Classification Search
CPC . A61B 5/055; A61B 5/1127; G01R 33/56509; G06T 5/003; G06T 2207/30196;
(Continued)

(56) References Cited

U.S. PATENT DOCUMENTS

| 10,660,541 B2 * | 5/2020 | Ernst ...................... G06F 18/214 |
| 2005/0137475 A1 * | 6/2005 | Dold ................ G01R 33/56509 600/420 |

(Continued)

FOREIGN PATENT DOCUMENTS

EP    3633401 A1    4/2020

OTHER PUBLICATIONS

European Search Report for European Application No. 20169738.0-1210 dated Oct. 12, 2020.
(Continued)

*Primary Examiner* — Andrae S Allison
*Assistant Examiner* — Emmanuel Silva-Avina
(74) *Attorney, Agent, or Firm* — Lempia Summerfield Katz LLC (57) ABSTRACT

The disclosure relates to a method for correcting a movement of an object occurring during an MR image acquisition. The method includes: determining a motion model describing possible movements of the object based on a defined number of degrees of freedom; detecting a motion of a marker provided on the object with a motion sensor; determining a description of the motion model in a common coordinate system; determining the motion of the marker in the common coordinate system; determining a first motion of the object in the common coordinate system using the description of the motion model, the first motion being the motion that best matches the determined motion of the marker in the common coordinate system using the defined number of degrees of freedom; and correcting the movement of the object based on the determined first motion in order to determine at least one motion corrected MR image.

18 Claims, 2 Drawing Sheets

(51) Int. Cl.
  *A61B 5/11* (2006.01)
  *G06T 7/73* (2017.01)
(52) U.S. Cl.
  CPC ...... *G06T 7/75* (2017.01); *G06T 2207/10088* (2013.01); *G06T 2207/30204* (2013.01)
(58) Field of Classification Search
  CPC . G06T 2207/30088; G06T 2207/20201; G06T 2200/04; G06T 2207/30204; G06T 2207/10088; G06T 7/75
  USPC .......................................................... 382/103
  See application file for complete search history.

(56) References Cited

U.S. PATENT DOCUMENTS

| | | | |
|---|---|---|---|
| 2005/0226527 A1 | 10/2005 | Weese et al. | |
| 2010/0054412 A1 | 3/2010 | Brinks et al. | |
| 2012/0268124 A1* | 10/2012 | Herbst | G01R 33/56509 324/309 |
| 2013/0188830 A1* | 7/2013 | Ernst | G01R 33/28 382/103 |
| 2017/0032538 A1 | 2/2017 | Ernst et al. | |
| 2017/0319143 A1* | 11/2017 | Yu | A61B 5/682 |
| 2018/0081376 A1* | 3/2018 | Zhang | G05D 3/12 |
| 2020/0110145 A1 | 4/2020 | Zeller | |

OTHER PUBLICATIONS

KinetiCor Biometric Intelligence Stand: https://kineticor.com/ Jun. 3, 2019. pp. 1-6.

Qin, L., et al. "Head movement correction for MRI with a single camera." Proceedings of the 16th Scientific Meeting, International Society for Magnetic Resonance in Medicine, Toronto, Canada. 2008. p. 1467.

Zaitsev, Maxim, et al. "Magnetic resonance imaging of freely moving objects: prospective real-time motion correction using an external optical motion tracking system." Neuroimage 31.3 (2006): 1038-1050.

Zaitsev, Maxim, et al. "Motion artifacts in MRI: A complex problem with many partial solutions." Journal of Magnetic Resonance Imaging 42.4 (2015): 887-901.

Gu, Songxiang, et al. "Improved motion correction in SPECT imaging using a non-rigid motion model." 2009 IEEE Nuclear Science Symposium Conference Record (NSS/MIC). IEEE, 2009. pp. 3242-3246.

* cited by examiner

CORRECTING OBJECT MOVEMENT DURING MR IMAGING

The present patent document claims the benefit of European Patent Application No. 20169738.0, filed Apr. 16, 2020, which is hereby incorporated by reference in its entirety.

TECHNICAL FIELD

The present application relates to a method for correcting a movement of an object occurring during a magnetic resonance (MR) image acquisition. Furthermore, the corresponding device is provided configured to correct the movement, a computer program, and a carrier including the computer program.

BACKGROUND

Magnetic resonance imaging is an imaging modality allowing a high-resolution generation of images of an object under examination such as a human being. Movements during the MR image acquisition, by way of example the respiratory movement of the object under examination or any other movement may result in artefacts, (e.g., types known as ghosting, blurring, and/or loss of intensity), in the generated image.

The breathing of the person under examination or any other movement may also be detected using external sensors such as a pneumatic cuff or based on signal processing of image signals generated by a camera monitoring the examined person. A camera-based motion correction identifies the motion in the generated images of the camera and tries to correct the motion in the image. These camera-based motion correction techniques may rely on a detection of a marker mounted at the examined object. The marker may have a Moiré pattern and the pattern is affected by the motion. However, this kind of motion correction may have the drawback that the marker is moving based on a skin movement as the examined human may feel irritated by the marker sticking to the skin such as the nose, or the nose may slightly move even when the examined part of the human such as the head is not moving. Further, any other skin movement such as a squinting movement or the alas of the nose may move during the inhalation or exhalation of the person during respiration.

When the movement of the marker is known, it is possible to determine the movement of the object during the MR image acquisition so that a movement correction may be carried out in real time in order to reduce the artefacts in the image. This may be a prospective correction of the movement or a retroactive correction.

Furthermore, it is possible to project a kind of pattern as marker onto the skin, wherein the movement of this pattern is recognized by the image sensor. However, here the same problem exists that the movement of the skin may not correspond to the movement of the object under examination. The object under examination may be the head or any part of the body such as the knee. If the motion of the object under examination is not correctly determined, the motion correction is also not reliable and does not provide satisfying results.

Accordingly, a need exists to overcome the above-mentioned problem and to be able to differentiate between an actual motion of the object occurring in the part of the object in which the MR signals are detected and a wrongly detected motion which is detected at the monitored marker or pattern on the surface, but which is not present at the actual part of the body from which the major part of the MR signals are detected for the image generation.

SUMMARY

The scope of the present disclosure is defined solely by the appended claims and is not affected to any degree by the statements within this summary. The present embodiments may obviate one or more of the drawbacks or limitations in the related art.

According to a first aspect, a method for correcting a movement of an object occurring during an MR image acquisition is provided in which the MR signals of the object are detected. According to one act of the method, a motion model is determined which describes the possible movements of the object based on a model function having a defined number of degrees of freedom the object is able to use for the movement. Furthermore, a motion of a marker is detected which is provided on the object wherein the motion is detected with a motion sensor. Furthermore, a description of the motion model is determined in a common coordinate system and the motion of the marker is determined in the common coordinate system. Furthermore, a first motion of the object is determined in the common coordinate system using the description of the motion model, wherein this first motion is the motion that best matches the determined motion of the marker in the common coordinate system using the defined number of degrees of freedom. Furthermore, the movement of the object is corrected based on the determined first motion in order to determine at least one motion corrected MR image.

The method above helps to discriminate a wrongly detected motion from an actual motion of the object under examination as it may be determined whether the detected motion of the marker is an actual motion which may be carried out by the object. As only a defined number of degrees of freedom is used in the common coordinate system, the first motion helps to determine the actual motion of the object under examination and helps to exclude motions which cannot occur in the object as a whole. The model function may be a complex mathematical function depending on all 6 degrees of freedom or depending on less than the possible 6 degrees of freedom. When the motion of the marker cannot be described with the defined number of degrees of freedom, it is likely that the object in total was actually not moving, only the part of the body to which the marker is attached or onto which the marker was projected. With this method, it is possible to differentiate between a movement of the part to which the marker is attached and an actual movement of the object. The object includes a region of interest in which the generated MR image may help in the generation of a diagnosis. The method helps to differentiate between a movement of a part of the object to which the marker is attached or where the marker is provided and movement of the region of interest within the object.

It is possible that for determining the motion of the marker, the motion of the marker is first determined in a marker coordinate system and the motion of the marker is then transferred to the common coordinate system. The common coordinate system may be the coordinate system of the marker, may be a coordinate system of the head or may be the coordinate system of the MR imaging system in which the MR signals are detected for determining a motion corrected MR image.

The first motion may be determined such that the first motion is described only using the defined number of degrees of freedom in the common coordinate system. The movement of the marker may occur in a movement period and for different points in time within the moving period, the movement of the marker is approximated with a corresponding best matching combination of the defined number of degrees of freedom describing the first motion which best matches the determined motion of the marker. This means that only movements are allowed which may be described using the defined motion model. Any other movement which cannot be described based on the defined motion model does not actually represent the movement of the object, but a movement of the marker which may be originating from a skin movement or a movement of the part of the body to which the marker is attached, by way of example the nose.

Furthermore, it is possible to determine the motion model based on the fact that the object has a defined maximum velocity allowed with which the object may change its position during the movement. With this maximum velocity, the inertia of the object may be considered.

The marker itself may be fixedly attached to the object or may also be projected onto the object, by way of example a grid projected onto the skin of the examined object.

The object may be the head of a human and the motion model has a total of three degrees of freedom, wherein the three degrees of freedom include two rotational degrees of freedom and one translational degree of freedom. This may reflect the situation when MR images are generated from a head of a human. When the head is positioned within the receiving coil, the different translational movements from the left side and right side or the translational movement in the anterior posterior direction may be hardly possible.

The two rotational degrees of freedom may include a nodding rotation of the head in the up down direction and a left right rotation of the head. The one translational degree of freedom may represent a cranial or a caudal movement of the head.

Furthermore, it is possible to consider which movement is more likely. Here, it is possible to weigh the two rotational degrees of freedom higher than the one translational degree of freedom. This may represent the assumption that the two rotational movements are occurring with a higher likelihood than the one translational movement in the cranial or caudal direction.

Furthermore, it is possible to determine the rotation axis for the left right rotation or a pivot point for the nodding rotation of the head based on object related data which are provided in the MR system which is configured to generate the MR image of the object. The object related data may include data obtained from the registration of the object such as the size, the weight, the age of the examined person or the position or the type of the detection coil used to detect the MR signals. Furthermore, it is possible to determine the rotation axis and the pivot point based on MR images which were obtained from the head of the examined person.

The motion of the marker may be detected using an image sensor as motion sensor which is not configured to detect the MR signal of the object. This means that an extra camera may be provided in the MR imaging system which monitors the examined person and the movement of the marker. In an alternative, the marker is part of the imaged body and MR signals/images are used to detect the motion of the examined person.

Furthermore, the defined number of degrees of freedom may be smaller than the possible six degrees of freedom which are possible for a rigid body motion, namely the three translational degrees of freedom and the three rotational degrees of freedom. As mentioned above, it is possible to consider only three degrees of freedom, four degrees of freedom, or five degrees of freedom depending on the situation of the examination. However, it is also possible to consider all six degrees of freedom which are possible for a rigid body motion.

A coordinate system may be chosen where the number of degrees of freedom may be reduced the most.

Furthermore, the corresponding device is provided configured to correct the movement of the object wherein the device includes at least one processing unit and a memory, wherein the memory contains instructions executable by the at least one processing unit. The device is operative to work as mentioned above or as described in further detail below.

Furthermore, a computer program is provided including a program code to be executed by at least one processing unit of the device, wherein execution of the program code causes the at least one processing unit to execute a method as discussed above or as discussed in further detail below.

Finally, a carrier is provided including the computer program wherein the carrier is one of an electronic signal, radio signal, optical signal, and computer readable storage medium.

The features mentioned above and features yet to be explained below may be used not only in the respective combinations indicated, but also in other combinations or in isolation without departing from the scope of the present disclosure. Features of the above-mentioned aspects and embodiments described below may be combined with each other in other combinations unless explicitly mentioned otherwise.

BRIEF DESCRIPTION OF THE DRAWINGS

The foregoing and additional features and effects of the application will become apparent from the following detailed description, when read in conjunction with the accompanying drawings in which like reference numerals refer to like elements.

DETAILED DESCRIPTION

In the following, embodiments of the disclosure will be described in detail with reference to the accompanying drawings. It is to be understood that the following description of embodiments is not to be taken in a limiting sense. The scope of the disclosure is not intended to be limited by the embodiments described hereinafter or by the drawings, which are to be illustrative only.

The drawings are to be regarded as being schematic representations, and elements illustrated in the drawings are not necessarily shown to scale. Rather, the various elements are represented such that their function and general purpose becomes apparent to a person skilled in the art. Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

As will be explained below, a method is provided in which the movement of a marker is monitored and it is checked whether the detected movement of the marker may be really based on a physical movement of the examined object or of the region of interest within the object or whether the detected movement of the marker may be based on a movement of another part of the examined object, to which the marker is attached and which has a negligible influence on the MR image generated from the MR signals, but not of the part of the object for which the MR signals are mainly detected. It is especially checked whether the object is able to carry out the detected movement of the marker taking into account a defined number of degrees of freedom the object is able to use for the movement. If it is detected that the detected movement of a marker cannot originate from the examined object, the corresponding part of the movement is excluded from the correction which might be used to generate a motion corrected MR image by using a description of the movement of the motion model which is only based on the defined number of degrees of freedom. The motion corrected MR image may be generated as known in prospective correction methods.

The disclosure is especially helpful in the MR imaging of the head as the head as rigid object may only carry out certain movements when it is placed in an MR imaging system and when a head coil is used to detect the MR signals. Accordingly, it is possible to differentiate between actual movements of the head and other movements which cannot have the basis in the movement of the head itself.

However, the present application is not restricted to an application in the head, other parts of the body such as the knee, the arm, or the shoulder may be used in a similar way.

Figure 1:
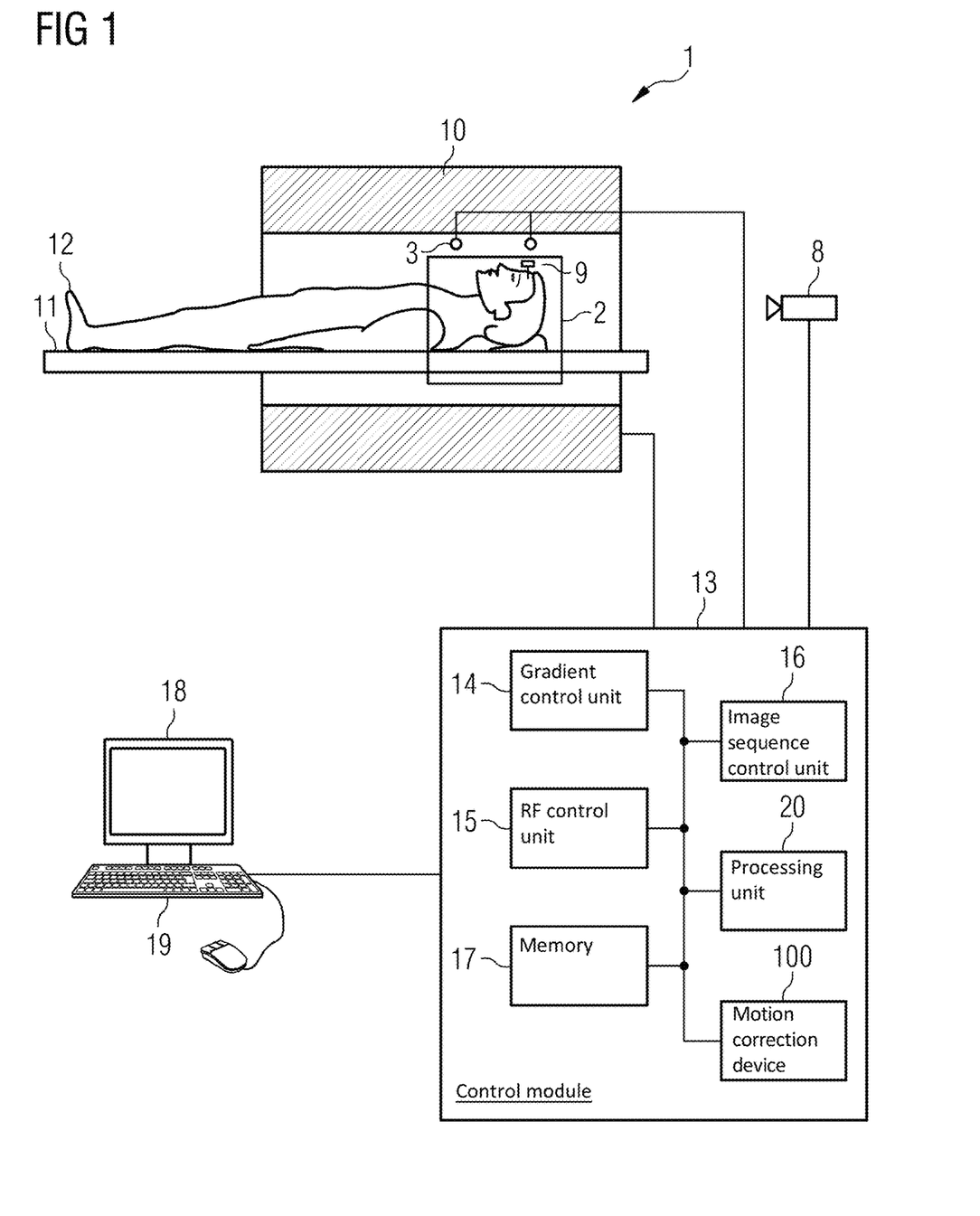
FIG. 1 depicts a schematic view of an example of a magnetic resonance (MR) system including a motion correction module configured to detect a motion and correct it.

FIG. 1 depicts a schematic view of an MR system 1 which includes a magnet 10 generating a polarization field B0. An object under examination 12, (e.g., a human being) lies on a table 11 and is moved into the center of the MR system 1 where MR signals after RF excitation may be detected by a receiving coil 2, which may include different coil sections. Each coil section may be associated with a corresponding detection channel. In the embodiment shown, two different detection channels 3 are used. By applying RF pulses and magnetic field gradients, the nuclear spins of the object 12, especially the part located in the receiving coil 2, are excited and the currents induced by the magnetization are detected. The way MR images are generated and how the MR signals are detected using a sequence of RF pulses and a sequence of magnetic field gradients are known in the art so that a detailed explanation thereof is omitted.

The MR system includes a control module 13, which is used for controlling the MR system 1. The control module 13 includes a gradient control unit 14 for controlling and switching the magnetic field gradients, an RF control unit 15 for controlling and generating the RF pulses for the imaging sequences. An image sequence control unit 16 is provided which controls the sequence of the applied RF pulses and magnetic field gradients and thus controls the gradient control unit 14 and the RF control unit 15. In a memory 17, computer programs needed for operating the MR system and the imaging sequences necessary for generating the MR images may be stored together with the generated MR images. The generated MR images may be displayed on a display 18, wherein an input unit 19 is provided used by a user of the MR system to control the functioning of the MR system. A processing unit 20 may coordinate the operation of the different functional units shown in FIG. 1 and may include one or more processors which may carry out instructions stored on the memory 17. The memory may include a suitable program code to be executed by the processing unit or by a motion correction device 100 configured to correct a motion of the object. Furthermore, a camera or image sensor 8 is shown in FIG. 1 which is configured to acquire picture data from the object 12. The generated picture data may be acquired with a frequency such that a movement of the examined object may be detected in the generated picture frames. By way of example, the frame rate of the generated picture frames may be between one and 100 frames per second. Furthermore, a marker 9 is attached to the object wherein the movement of the marker is used to deduce the movement of the head itself. In the embodiment shown, an external marker is attached to the examined body. However, it is also possible that a part of the examined body itself is the marker and the position or motion of the marker may be determined with an external image sensor or may be determined based on the generated MR images, e.g. using navigator images generated to detect the motion. The position or movement, determined based on the marker, may also be determined using a certain accuracy, such that possible motions are included with are not possible with the determined motion model. The motion model may then help to only consider motions which may be explained based on the model with the selected model function.

The picture data may be processed either by the processing unit 20 or by the device 100 in order to detect a motion of the object 12 during a time period when the MR signals are detected. In the embodiment shown the processing unit 20 and the device 100 for determining and correcting a movement of the object 12 are separate entities. However, the functions provided by these two entities may be implemented in a single entity or may be implemented by a cloud environment.

Figure 2:
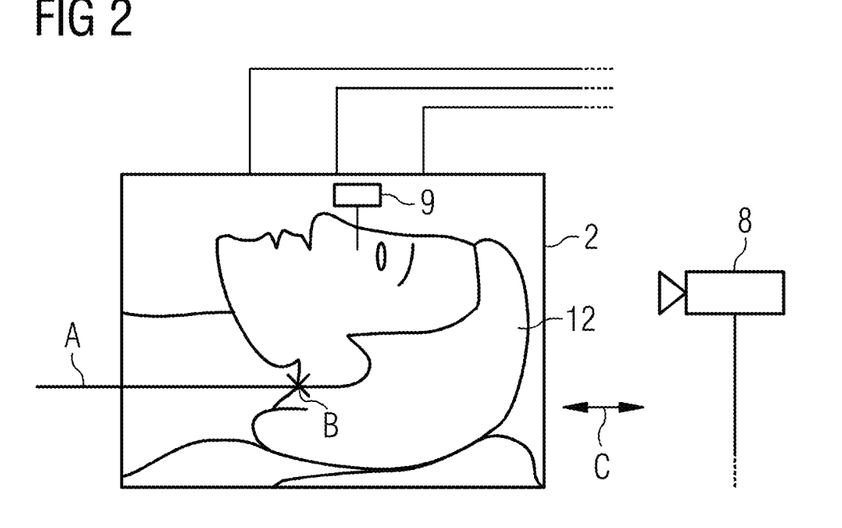
FIG. 2 depicts a schematic view of an example of a generation of an MR image of the head of a person wherein a marker is attached to the head in order to detect the motion of the head in order to generate motion corrected MR images.

FIG. 2 depicts in more detail how a person as object 12 is examined wherein the head is examined using a head coil as receiver coil 2. In the embodiment shown, the head coil includes three different coil sections. In other embodiments, more or less receiving channels might be used. Attached to the nose of the person 12 is the marker 9. The movement of this marker is detected by the image sensor 8. However, the marker may also move when the skin is moving to which the marker is attached, by way of example the nose. The head may not move in all different directions and furthermore it may be assumed that the head may only carry out rigid body transformations. Based on a rotation point of the head on the support structure on which the head is positioned, different nonlinear movements of the head may be expected. The model function may be fitted to the detected motion of the marker in order to determine the motion that may be explained on the used model function, wherein the model function may be any function, e.g., a linear or non-linear function.

All movements of the marker 9 which do not fit to a common and typical and possible movement of the head may be filtered out and are not considered for the correction of the movement of the head.

One possible implementation is as follows:

In a first act, a motion model is determined which describes the possible movements of the examined object, here the head. A simple model may assume that the head may only rotate around an axis A which is parallel to the spine, which may be considered as a left right rotation from the point of view of the person. Furthermore, it may be assumed that only a nodding rotation is allowed around a pivot point B shown in FIG. 2. In addition to these two rotational degrees of freedom, one translational degree of freedom may be considered such as the translation in the cranial caudal direction as indicated by arrow C.

Accordingly, it is assumed that only a defined number of movements are possible, which are a superposition of the possible movements allowed by the different degrees of freedom as specified above. Any other movement which cannot be described with these defined number of degrees of freedom cannot originate from the head itself but may originate from a movement of the part of the body to which the marker 9 is attached.

The motion model may be determined in a coordinate system of the head or in a coordinate system of the MR imaging system.

The marker may have its own coordinate system. As the movement of the marker is determined to deduce the movement of the head, the movement of the marker and the motion model have to be described in a common coordinate system. The common coordinate system may be any suitable coordinate system, be it the coordinate system of the MR system, the coordinate system of the marker, the coordinate system of the head of the user, or any other coordinate system suited for describing the used motion model. This includes polar, cylindrical, and spherical coordinate systems, such as more complex warped coordinate systems.

In a further act, the motion model is transferred into this common coordinate system. Furthermore, the motion of the marker is determined in the common coordinate system. When both the motion model and the movement of the marker are determined in a common coordinate system, it is possible to determine for each point in time a status of the defined set of the number of degrees of freedom which best describe the determined movement of the marker as determined based on the images generated by camera 8. This means that a first motion is determined using only the description of the motion model with the defined number of degrees of freedom. This first motion is a combination of motions defined by the defined set of degrees of freedom. This first motion is the motion which best matches the actual motion of the marker as determined from the images. This is a kind of matching procedure in which different combinations of the different movements allowed by the different degrees of freedom are combined in order to generate a movement which best fits to the detected movement of the marker. This matching may be implemented as a least square fit, however, any other minimization method might be used which minimizes the difference between the motion as determined for the marker based on the images and as determined using the motion model which is only based on a certain number of degrees of freedom in the common coordinate system. When this first motion of the object as described by the motion model is determined, it is possible to use this first motion as the actual motion of the object, here of the head, this first motion is then used for the motion corrected MR images. One possible implementation for generating motion corrected MR images is disclosed in M. Zaitsev, C. Dold, G. Sakas, J. Hennig, and O. Speck "Magnetic resonance imaging of freely moving objects: Prospective real-time motion correction using an external optical motion tracking system"; NeuroImage 31 (2006) 1038-1050.

When the first motion is known in the common coordinate system, it might be necessary to transform this first motion into the coordinate system of the MR system, wherein this first motion is then used to generate motion correct MR images as known in the art. In the present case motion and movement are used interchangeably.

Furthermore, it is possible to consider further degrees of freedom such as all six degrees of freedom. Additionally, is possible to consider a maximum speed that is possible for the movement of the examined object, here the head. Based on the inertia of the head certain movements such as very fast movements may not be possible.

The rotation axis such as the rotation axis A or the pivot point B shown in FIG. 2 may be determined based on MR images which were generated from the head. Furthermore, it is possible to use additional data which are known from the examined person such as the size, the weight, the age, and/or the type or the position or the inclination of the coil in which the object is located.

Figure 3:
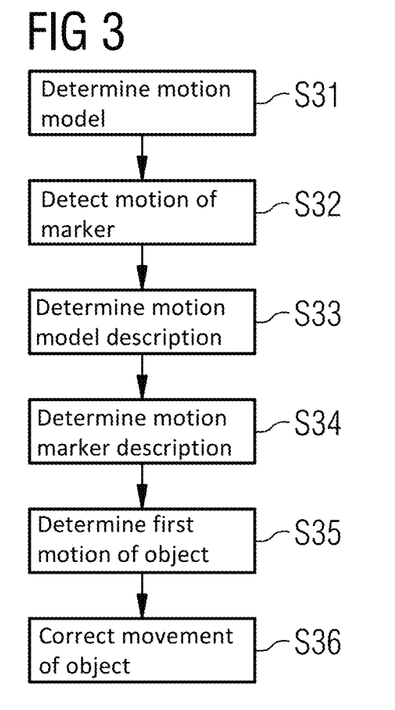
FIG. 3 depicts an example schematic view of a flowchart of a method carried out by a device configured to correct a movement of an object.

FIG. 3 summarizes some of the main acts carried out by the motion correction device 100 shown in FIG. 1 when determining a correction of the motion. In act S31, a motion model is determined using a model function which describes the possible movements of the object based on a defined number of degrees of freedom the object is able to use for the movement, or a more generalized mathematical description thereof. In the example above, only three possible degrees of freedom were considered. However, this may depend on the application and the part of the body for which the imaging system is used. In act S32, the motion of the marker is detected which is provided on the object. The marker may be a marker which is attached to the object such as the marker 9 shown in FIG. 3. However, the marker may also be a grid projected onto the object. In a further act S33, a description of the motion model in a common coordinate system is determined and, in step act S34, the motion of the marker in the common coordinate system. When the motion model and the motion of the marker are known in the common coordinate system, it is possible to determine, in act S35, a first motion of the object in the common coordinate system only using the description of the motion model and which best matches the determined motion of the marker. In act S36, the movement of the object is then used for the correction of the movement of the object, wherein the first motion which only considers certain degrees of freedom is used in order to generate the motion corrected MR images.

Figure 4:
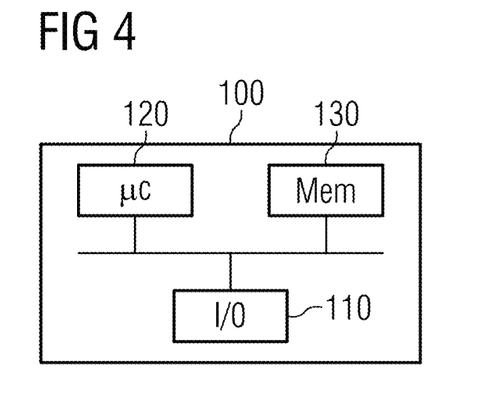
FIG. 4 depicts an example schematic architectural view of the device configured to correct the movement of the object.

FIG. 4 depicts a schematic architectural view of a motion correction device 100 which may carry out the above discussed correction of the movement. The device 100 may be a separate entity or may be implemented as part of a common processing unit within or outside the MR system 1. The device 100 includes an interface or input/output 110 which is used to receive user data such as MR images or control messages and used to transmit user data or control messages to other entities, such as the motion corrected MR images generated by the device 100. The device 100 furthermore includes a processing unit one 120 which is responsible for the operation of the motion correction device 100 as discussed above. The processing unit 120 may include one or more processors used to carry out instructions stored on a memory 130 wherein the memory may be a part of the memory 17 discussed above or may be separate memory. The memory may include a read-only memory, a random-access memory, a mass storage, a hard disk, or the like. The memory may furthermore include a suitable program code to be executed by the processing unit 120 so as to implement the above-described functionality in which the motion correction device 100 is involved.

The above-described method provides an improved motion correction as only the possible motions are considered and other motions which cannot be carried out by the corresponding object are filtered out and are not considered for the motion correction.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

Although the disclosure has been illustrated and described in detail with the exemplary embodiments, the disclosure is not restricted by the examples disclosed and other variations may be derived therefrom by a person skilled in the art without departing from the protective scope of the disclosure.

The invention claimed is:

1. A method for correcting a movement of an object occurring during a magnetic resonance (MR) image acquisition in which MR signals of the object are detected, the method comprising:
   determining a motion model describing possible movements of the object based on a model function having a defined number of degrees of freedom the object is able to use for the movement, wherein the defined number of degrees of freedom of the object is less than all six degrees of freedom possible for rigid body motion;
   detecting a motion of a marker provided on the object with a motion sensor;
   checking whether the object is configured to carry out the detected motion of the marker taking into account the defined number of degrees of freedom the object is able to use for the movement;
   determining a description of the motion model in a common coordinate system having the defined number of degrees of freedom;
   determining the motion of the marker in the common coordinate system;
   determining a first motion of the object in the common coordinate system using the description of the motion model, wherein the first motion is a motion that best matches the determined motion of the marker in the common coordinate system using only the defined number of degrees of freedom; and
   correcting the movement of the object based on the determined first motion in order to determine at least one motion corrected MR image, wherein a corresponding part of the detected motion of the marker is excluded from the correction when the checking identifies that the detected motion of the marker does not originate from the defined number of degrees of freedom of the object.

2. The method of claim 1, wherein the determining of the motion of the marker comprises determining the motion of the marker in a marker coordinate system, and
   wherein the motion of the marker is transferred to the common coordinate system.

3. The method of claim 1, wherein the first motion is determined such that the first motion is described only using the defined number of degrees of freedom in the common coordinate system, and
   wherein the movement of the marker is occurring in a movement period, and for different points in time within the movement period, the movement of the marker is approximated with a corresponding best matching combination of the defined number of degrees of freedom describing the first motion which best matches the determined motion of the marker.

4. The method of claim 3, wherein the object is head of a human, and
   wherein the motion model has a total of three degrees of freedom with two rotational degrees of freedom and one translational degree of freedom.

5. A method for correcting a movement of an object occurring during a magnetic resonance (MR) image acquisition in which MR signals of the object are detected, the method comprising:
   determining a motion model describing possible movements of the object based on a model function having a defined number of degrees of freedom the object is able to use for the movement;
   detecting a motion of a marker provided on the object with a motion sensor;
   determining a description of the motion model in a common coordinate system;
   determining the motion of the marker in the common coordinate system;
   determining a first motion of the object in the common coordinate system using the description of the motion model, wherein the first motion is a motion that best matches the determined motion of the marker in the common coordinate system using the defined number of degrees of freedom; and
   correcting the movement of the object based on the determined first motion in order to determine at least one motion corrected MR image,
   wherein the object is head of a human,
   wherein the motion model has a total of three degrees of freedom with two rotational degrees of freedom and one translational degree of freedom, and
   wherein, in the determining of a best matching combination of the three degrees of freedom, the two rotational degrees of freedom are weighted higher than the one translation degree of freedom.

6. The method of claim 4, wherein the two rotational degrees of freedom comprise a nodding rotation of the head in an up-down direction and a left-right rotation of the head, and
   wherein the one translation degree of freedom comprises a cranial caudal movement of the head.

7. The method of claim 6, further comprising:
   determining a rotation axis for the left-right rotation and a pivot point for the nodding rotation of the head based on object related data provided in an MR system configured to generate the MR image of the object.

8. The method of claim 7, wherein the rotation axis and the pivot point are determined based on MR images obtained from the head.

9. The method of claim 1, wherein the motion model is determined based on the object having a defined maximum velocity allowed to change a position of the object during the movement.

10. The method of claim 1, wherein the marker is fixedly attached to the object or is projected onto the object.

11. The method of claim 1, wherein the object is head of a human, and
wherein the motion model has a total of three degrees of freedom with two rotational degrees of freedom and one translational degree of freedom.

12. A method for correcting a movement of an object occurring during a magnetic resonance (MR) image acquisition in which MR signals of the object are detected, the method comprising:
determining a motion model describing possible movements of the object based on a model function having a defined number of degrees of freedom the object is able to use for the movement;
detecting a motion of a marker provided on the object with a motion sensor;
determining a description of the motion model in a common coordinate system;
determining the motion of the marker in the common coordinate system;
determining a first motion of the object in the common coordinate system using the description of the motion model, wherein the first motion is a motion that best matches the determined motion of the marker in the common coordinate system using the defined number of degrees of freedom; and
correcting the movement of the object based on the determined first motion in order to determine at least one motion corrected MR image,
wherein the object is head of a human,
wherein the motion model has a total of three degrees of freedom with two rotational degrees of freedom and one translational degree of freedom,
wherein the two rotational degrees of freedom comprise a nodding rotation of the head in an up-down direction and a left-right rotation of the head, and
wherein the one translation degree of freedom comprises a cranial caudal movement of the head.

13. The method of claim 12, further comprising:
determining a rotation axis for the left-right rotation and a pivot point for the nodding rotation of the head based on object related data provided in an MR system configured to generate the MR image of the object.

14. The method of claim 13, wherein the rotation axis and the pivot point are determined based on MR images obtained from the head.

15. The method of claim 1, wherein the motion of the marker is detected using an image sensor as the motion sensor which is not configured to detect the MR signals of the object.

16. A device configured to correct a movement an object occurring during a magnetic resonance (MR) image acquisition in which MR signals of the object are detected, the device comprising:
at least one processing unit; and
a memory comprising instructions, when executed by the at least one processing unit, cause the device to:
determine a motion model describing possible movements of the object based on a defined number of degrees of freedom the object is able to move, wherein the defined number of degrees of freedom of the object is less than all six degrees of freedom possible for rigid body motion;
detect a motion of a marker provided on the object with a motion sensor;
determine a description of the motion model in a common coordinate system having the defined number of degrees of freedom;
determine the motion of the marker in the common coordinate system;
determine a first motion of the object in the common coordinate system using the description of the motion model, wherein the first motion is a motion that best matches the determined motion of the marker in the common coordinate system using only the defined number of degrees of freedom; and
correct the movement of the object based on the determined first motion in order to determine at least one motion corrected MR image,
wherein the object is head of a human,
wherein the motion model has a total of three degrees of freedom with two rotational degrees of freedom and one translational degree of freedom,
wherein the two rotational degrees of freedom comprise a nodding rotation of the head in an up-down direction and a left-right rotation of the head, and
wherein the one translation degree of freedom comprises a cranial caudal movement of the head.

17. The device of claim 16, wherein the first motion is determined such that the first motion is described only using the defined number of degrees of freedom in the common coordinate system, and
wherein the movement of the marker is occurring in a movement period, and for different points in time within the movement period, the movement of the marker is approximated with a corresponding best matching combination of the defined number of degrees of freedom describing the first motion which best matches the determined motion of the marker.

18. A non-transitory computer program comprising program code to be executed by at least one processor of a device, wherein execution of the program code by the at least one processor causes the device to:
determine a motion model describing possible movements of an object undergoing a magnetic resonance (MR) image acquisition based on a defined number of degrees of freedom the object is able to move, wherein the defined number of degrees of freedom of the object is less than all six degrees of freedom possible for rigid body motion;
detect a motion of a marker provided on the object with a motion sensor;
determine a description of the motion model in a common coordinate system;
determine the motion of the marker in the common coordinate system having the defined number of degrees of freedom;
determine a first motion of the object in the common coordinate system using the description of the motion model, wherein the first motion is a motion that best matches the determined motion of the marker in the common coordinate system using only the defined number of degrees of freedom; and
correct a movement of the object based on the determined first motion in order to determine at least one motion corrected MR image,
wherein the object is head of a human,
wherein the motion model has a total of three degrees of freedom with two rotational degrees of freedom and one translational degree of freedom,
wherein the two rotational degrees of freedom comprise a nodding rotation of the head in an up-down direction and a left-right rotation of the head, and wherein the one translation degree of freedom comprises a cranial caudal movement of the head.

\* \* \* \* \*